(12) United States Patent
Hawman

(10) Patent No.: US 7,847,257 B2
(45) Date of Patent: Dec. 7, 2010

(54) TOMOGRAPHIC SAMPLING FOR SPECT WITH CONE-BEAM OR MULTIFOCAL COLLIMATION

(75) Inventor: Eric Grant Hawman, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 23 days.

(21) Appl. No.: 12/062,847

(22) Filed: Apr. 4, 2008

(65) Prior Publication Data

US 2009/0250617 A1 Oct. 8, 2009

(51) Int. Cl.
*G01T 1/166* (2006.01)
(52) U.S. Cl. .................................. 250/363.05
(58) Field of Classification Search ............ 250/363.04, 250/363.05, 363.08
See application file for complete search history.

(56) References Cited

U.S. PATENT DOCUMENTS

| | | | | |
|---|---|---|---|---|
| 4,476,389 A | * | 10/1984 | Ueyama et al. | 250/363.05 |
| 4,670,657 A | | 6/1987 | Hawmann | |
| 2004/0262525 A1 | * | 12/2004 | Yunker et al. | 250/363.08 |
| 2005/0269514 A1 | * | 12/2005 | Stark | 250/363.08 |

* cited by examiner

*Primary Examiner*—Constantine Hannaher
(74) *Attorney, Agent, or Firm*—Peter L. Kendall

(57) ABSTRACT

An apparatus and method for nuclear medical imaging (e.g., SPECT imaging) using cone-beam or multifocal collimators is disclosed. According to the embodiment of the invention, the detector/collimator is tilted in a fore-aft direction, with the tilt angle varying as a function of the orbital position of the detector assembly. The patient pallet may also be moved longitudinally as a function of the tilt angle (i.e., as a function of the orbital position) for optimal image quality.

13 Claims, 3 Drawing Sheets

TOMOGRAPHIC SAMPLING FOR SPECT WITH CONE-BEAM OR MULTIFOCAL COLLIMATION

TECHNICAL FIELD

In general, an embodiment of the present invention relates to nuclear medical imaging. More particularly, an embodiment of the invention relates to SPECT imaging with cone-beam or multifocal collimation.

BACKGROUND

It has been shown that SPECT reconstruction when using cone-beam or multifocal (cardiofocal) collimators is subject to "cone-beam" type artifacts. These artifacts are easily recognized using a Defrise phantom, which consist of a series of hot and cold plates arranged along the axis of rotation. They occur because in local regions away from the central midplane, neither the Orlov nor the Tuy sampling completeness criteria are satisfied for either circular or non-circular camera orbits in a plane perpendicular to the axis of rotation. As a consequence, spatial frequency components around the axial direction are not well determined. This may cause degradation of spatial resolution in the axial direction as well as some spatial distortions. In Defrise phantom images, such artifacts are readily recognized; however, with clinical cardiac images, artifacts may be hard to recognize, and their presence reduces the accuracy of image interpretation.

Furthermore, statistically based image reconstruction such as MLEM or OSEM may be somewhat more tolerant to sampling incompleteness (when using cone-beam or multifocal collimation) than FBP. Still, however, there is significant degradation from incomplete sampling.

SUMMARY

A SPECT apparatus and method are disclosed to overcome sampling incompleteness when using cone-beam or multifocal collimation. According to an embodiment of the invention, a SPECT detector with a cone-beam or multifocal collimator is tilted in a fore-aft direction as the camera head orbits about a patient, with the tilt angle varying as a function of the position of the detector along its orbital trajectory. Additionally, the patient may be moved longitudinally as the camera head orbits and tilts, as a function of the fore-aft tilt angle, so as to achieve optimal image quality.

Thus, in one aspect, an embodiment of the invention features apparatus for nuclear imaging of a patient. Such apparatus includes a patient support pallet; a nuclear medical imaging head supported for orbital movement relative to the patient support pallet about an orbital axis; and a control system. The imaging head includes a detector and a collimator. The control system is configured to control the orbital movement of the imaging head and to control a tilt angle $\phi$ of the detector and the collimator so as to vary as a function of the orbital angular position $\theta$ of the imaging head.

In specific embodiments, the apparatus is a SPECT system, and the collimator may be a cone-beam collimator or a multifocal collimator. Other collimation possiblities for which this sampling method would be useful are astigmatic collimation (see U.S. Pat. No. 4,670,657, incorporated herein by reference) two-dimension diverging collimation, or other type of collimations which are non-parallel with respect to the axial direction. The imaging head may be configured to tilt as a whole, or the detector and collimator may be arranged to tilt relative to the imaging head housing. Suitably, the patient support pallet moves longitudinally, with the amount of movement varying as a function of the orbital position of the imaging head.

In another aspect, an embodiment of the invention features a method for imaging a patient using nuclear medicine. Such method includes disposing the patient on a patient support pallet; orbiting a nuclear medical imaging head relative to the patient and about a longitudinal axis, which nuclear medical imaging head includes a detector and a collimator; and tilting the detector and the collimator in a longitudinal, fore/aft direction as a function of the orbital angular position $\theta$ of the imaging head.

In specific embodiments, the method may include tilting the imaging head as a whole; alternatively, the method may include tilting the detector and the collimator relative to the imaging head housing. Suitably, the patient is also moved longitudinally as a function of the orbital position of the imaging head and hence as a function of the detector/collimator tilt angle.

BRIEF DESCRIPTION OF THE DRAWINGS

Embodiments of the invention will now be described in greater detail in the following by way of example only and with reference to the attached drawings, in which.

DETAILED DESCRIPTION

Figure 1:
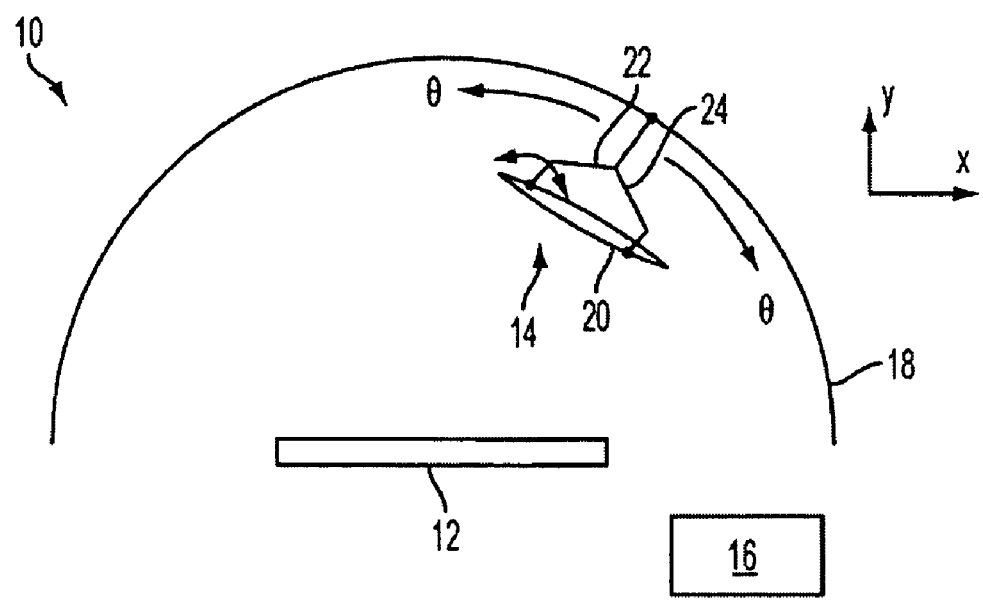
FIG. 1 is a schematic axial (end) view of a nuclear medical imaging system according to an embodiment of the invention.
Figure 2:
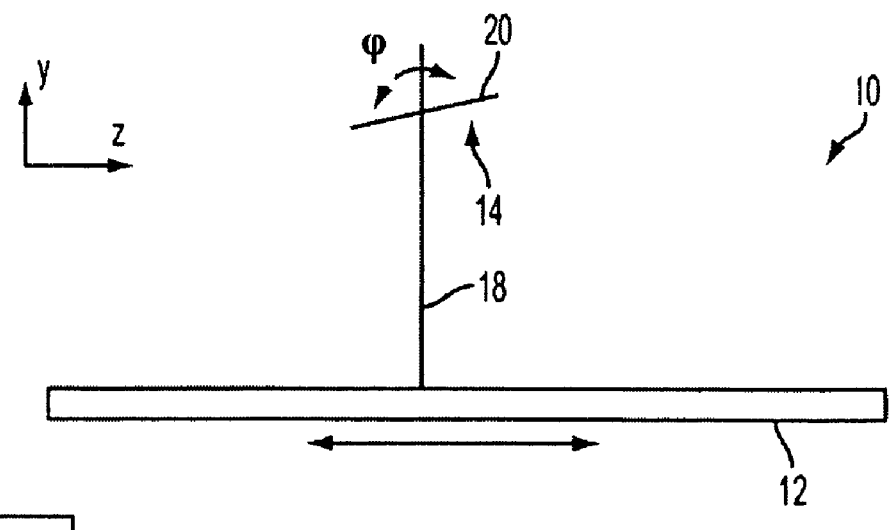
FIG. 2 is a schematic side view of a nuclear medical imaging system according to an embodiment of the invention.

In general, a nuclear medical imaging system 10 according to an embodiment of the invention, e.g., a SPECT system, is illustrated in FIGS. 1-6. As illustrated in FIGS. 1 and 2, the system 10 includes a pallet 12 on which a patient is supported during imaging; a nuclear medical imaging head 14, e.g., a scintillation camera used for SPECT imaging; and a computer-based control system 16, which is programmed to control movement of the imaging system components and image acquisition.

To position the patient, the pallet 12 moves longitudinally, i.e., in the z-direction, which is aligned with the head-to-foot orientation of the patient's body. Additionally, the imaging head 14 orbits about the pallet 12 (e.g., circularly, elliptically, etc.), with the central orbital axis oriented in the z-direction and the orbital angle denoted by $\theta$. To accommodate such orbital movement, the imaging head 14 is supported by a track, gantry, gimbal, armature, etc., as is known in the art and indicated schematically as 18.

Figure 3:
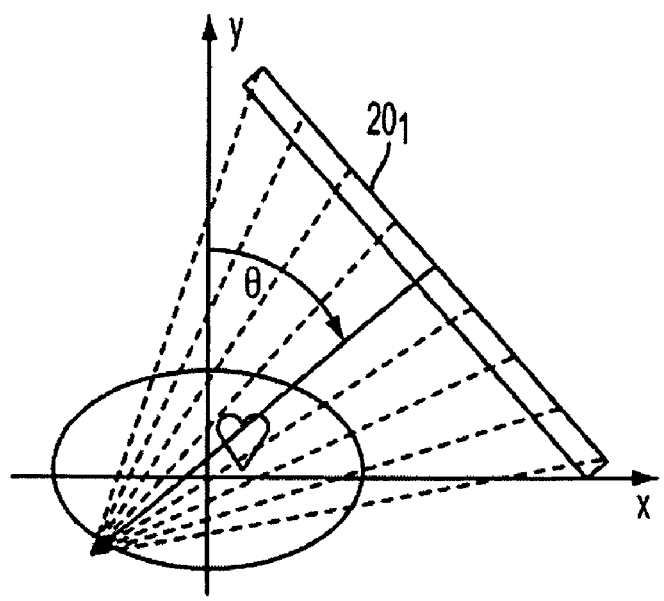
FIGS. 3 and 4 are schematic axial (end) and top (anterior) views of a nuclear medical imaging system as shown in FIGS. 1 and 2, using a cone-beam collimator.
Figure 4:
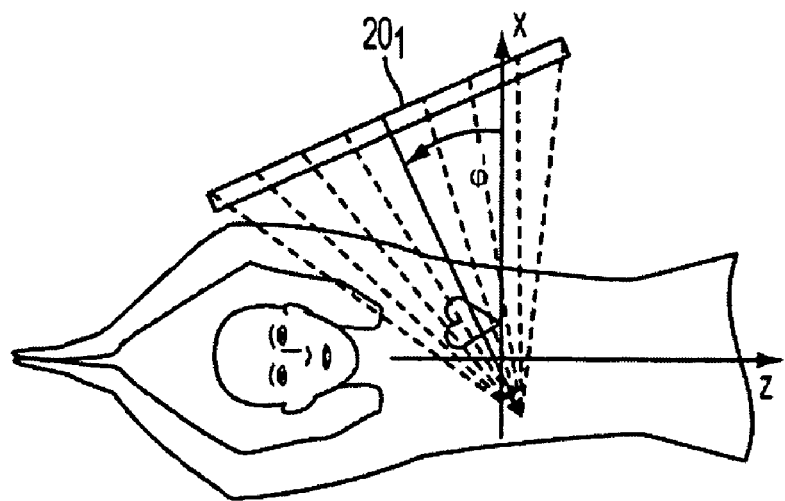
Figure 5:
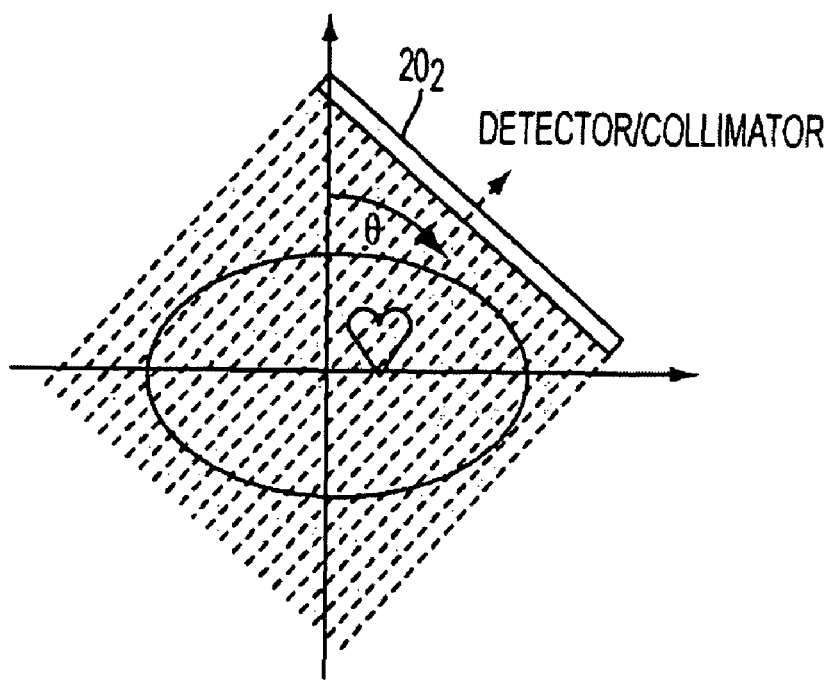
FIGS. 5 and 6 are schematic axial (end) and top (anterior) views of a nuclear medical imaging system as shown in FIGS. 1 and 2, using a multifocal collimator.
Figure 6:
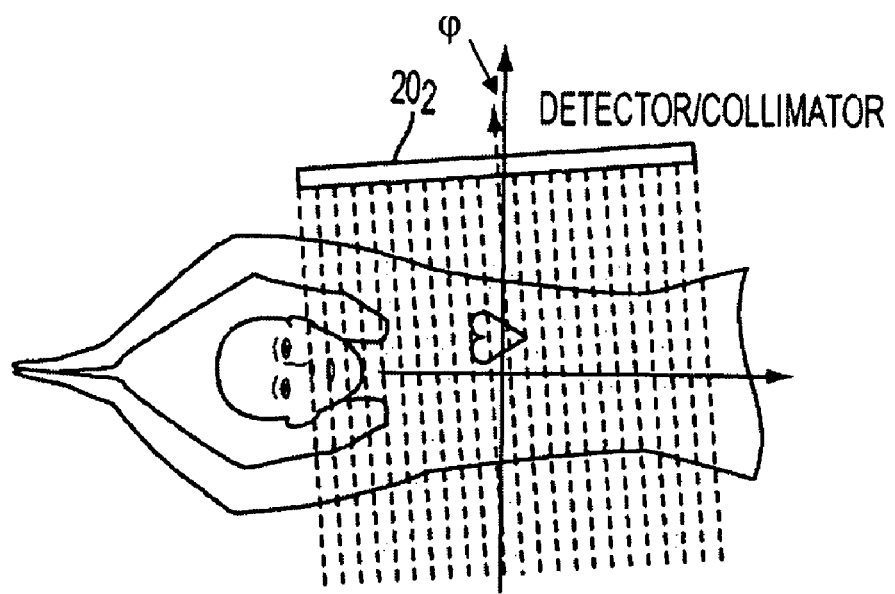

Furthermore, the imaging head 14 includes a planar scintillation detector and a planar collimator, which are generally parallel and in close proximity to each other. They are denoted collectively and schematically in the Figures as element number 20. In one embodiment of the invention, illustrated in FIGS. 3 and 4, the collimator is a cone-beam collimator, and the combination detector/collimator is denoted as element number $20_1$. In an alternate embodiment of the invention, illustrated in FIGS. 5 and 6, the collimator is a multifocal collimator, and the combination detector/collimator is denoted as element number $20_2$. According to an embodiment of the invention, the detector/collimator 20 can be z-axially tilted in a fore-aft manner, with the tilt angle toward the patient's head or toward the patient's feet denoted by φ, as illustrated in FIGS. 2, 4, and 6. (It should be noted that FIG. 2 depicts the imaging head 14 at the highest point in its orbit (θ=0), such that the detector/collimator 20 is viewed perfectly edge-on in that Figure.) This tilting of the detector/collimator can be accomplished by tilting the entire imaging head 14 in embodiments where the detector/collimator is fixed relative to the rest of the components of the imaging head 14 (e.g., the imaging head's housing). Alternatively, it is envisioned that embodiments can be provided in which the detector/collimator can be tilted relative to the rest of the components of the imaging head 14 (e.g., the imaging head's housing). Either type of embodiment is illustrated schematically by FIG. 1, in which pivot support arms 22 can be located external to the housing of the imaging head 14 so as to allow the entire imaging head 14 to tilt fore and aft or, alternatively, they (pivot support arms 22) can be located within the housing of the imaging head 14 so as to allow just the detector/collimator to tilt fore and aft.

More specifically according to an embodiment of the invention, the detector/collimator tilt angle φ is controlled by the control system 16 so as to vary as a function of the orbital angle θ (i.e., $\phi=\phi(\theta)$). For example, to achieve complete sampling for reconstruction during SPECT acquisition with a cone-beam collimator as illustrated in FIGS. 3 and 4, some of the rays that pass through each point in the reconstruction must be perpendicular to the gantry orbital axis (the z-axis). Over the entire orbital range $[-\theta_{max}, \theta_{max}]$, the detector/collimator $20_1$, is progressively tilted over an angular range $[\phi=-\alpha_{max}, \phi=\alpha_{max}]$, where $\alpha_{max}$ is the half collimator cone angle. Accordingly, for every point to be reconstructed, there will be some rays detected that are perpendicular to the gantry axis of rotation.

Similarly, the same inventive tilting of the detector/collimator as a function of the orbital angle θ (i.e., $\phi=\phi(\theta)$) is applied when imaging using a multifocal collimator. (As is known in the art, the focal length of a multifocal collimator is a function of the lateral coordinate x, i.e., $F(x)=f_S+(f_L-f_S)*(x/w)^4$, where $f_S$ and $f_L$ are short and long focal lengths, respectively, and w is the half width of the camera field of view. A similar relation holds for the focusing geometry in the y-dimension of the camera as well.) In this case, over the entire orbital range $[-\theta_{max}, \theta_{max}]$, the detector/collimator $20_2$ is progressively tilted over an angular range $[\phi=-\alpha_{max}, \phi=\alpha_{max}]$, where $\alpha_{max}$ is the maximum deviation in the axial direction (or transverse direction) for the collimator rays (holes) from orthogonality to the collimator surface. Accordingly, for every point to be reconstructed, there will be some rays that are perpendicular to the gantry axis of rotation (orbital axis).

Furthermore, according to an embodiment of the invention, it is advantageous for optimal image quality to move the pallet 12 longitudinally as a function of the detector/collimator tilt angle φ and the radius R of the detector/collimator from the orbital axis, so that the target organ (e.g., the heart, as shown in FIGS. 3-6) remains centered with respect to the mid-plane of the detector/collimator. For example, if the tilt angle φ is such that the gamma-ray-receiving face of the detector/collimator is oriented toward the patient's feet, then the pallet would be shifted toward the patient's feet by an amount $\delta=R \tan(\phi(\theta))$. Conversely, if the detector/collimator is tilted toward the patient's head, then the pallet would be shifted toward the patient's head. Such movement of the pallet as a function of the detector/collimator tilt angle may be employed with either disclosed embodiment (cone-beam collimator or multifocal collimator).

Finally, it is also advantageous for the signal-to-noise ratio of the image if the dwell time for each view is selected such that the three-dimensional spatial frequency components of the object of interest receive equal weighting. Such weighting of the dwell time may take into account the three-dimensional density for sampling of the spatial frequency component, object attenuation, and system resolution.

While the disclosure has been disclosed with reference to specific exemplary embodiments, modifications to and departures from the disclosed embodiments will occur to those having skill in the art. Accordingly, what is protected is defined by the scope of the following claims.

What is claimed is:

1. A nuclear medical imaging apparatus, comprising:
   a patient support pallet;
   a nuclear medical imaging head supported for orbital movement relative to the patient support pallet about an orbital axis, the imaging head including a detector and a non-parallel hole collimator arranged parallel to each other, the imaging head being configured such that the detector and the collimator can be tilted in a longitudinal, fore/aft direction by a tilt angle φ; and
   a control system that is configured to control the orbital movement of the imaging head about said patient support pallet over a predetermined range of orbital angular positions θ and to control the tilt angle φ so as to vary as a function of the orbital angular position θ of the imaging head, in such manner that for each orbital position being imaged, nuclear emission rays are detected that are perpendicular to said orbital axis.

2. The nuclear medical imaging apparatus of claim 1, wherein said nuclear medical imaging apparatus is a SPECT system.

3. The nuclear medical imaging apparatus of claim 1, wherein said collimator is a cone-beam collimator.

4. The nuclear medical imaging apparatus of claim 1, wherein said collimator is an astigmatic collimator.

5. The nuclear medical imaging apparatus of claim 1, wherein said collimator is a two-dimensional diverging collimator.

6. The nuclear medical imaging apparatus of claim 1, wherein said collimator is a multifocal collimator.

7. The nuclear medical imaging apparatus of claim 1, wherein the imaging head comprises a housing; the detector and the collimator are fixed relative to the housing; and the entire imaging head can be tilted in the longitudinal, fore/aft direction.

8. The nuclear medical imaging apparatus of claim 1, wherein the imaging head comprises a housing and the detector and the collimator can be tilted relative to the housing.

9. The nuclear medical imaging apparatus of claim 1, wherein the patient support pallet is moveable in the longitudinal direction and wherein the control system is configured to control movement of the patient support pallet as a function of the orbital angular position θ of the imaging head and hence as a function of the tilt angle φ of the detector and the collimator.

10. A method for imaging a patient, comprising:
   disposing the patient on a patient support pallet along a longitudinal axis;
   orbiting a nuclear medical imaging head relative to the patient and about said longitudinal axis over a predetermined range of orbital angular positions θ, the nuclear medical imaging head including a detector and a non-parallel hole collimator; and tilting the detector and the collimator in a longitudinal, fore/aft direction by a tilt angle $\phi$ that varies as a function of the orbital angular position $\theta$ of the imaging head, in such manner that for each orbital position being imaged, nuclear emission rays are detected that are perpendicular to said orbital axis.

11. The method of claim 10, wherein the imaging head is tilted as a whole in the longitudinal, fore/aft direction.

12. The method of claim 10, wherein the detector and the collimator are tilted relative to a housing of the imaging head.

13. The method of claim 10, further comprising moving the patient longitudinally as a function of the orbital angular position $\theta$ of the imaging head and hence as a function of the tilt angle $\phi$ of the detector and the collimator.

* * * * *